| United States Patent [19] | [11] Patent Number: 4,866,745 |
|---|---|
| Akai | [45] Date of Patent: Sep. 12, 1989 |

[54] ULTRAHIGH SPEED X-RAY CT SCANNER

[75] Inventor: Makoto Akai, Ibaraki, Japan

[73] Assignee: Agency of Industrial Science & Technology, Ministry of International Trade & Industry, Tokyo, Japan

[21] Appl. No.: 31,666

[22] Filed: Mar. 30, 1987

[30] Foreign Application Priority Data

Jul. 16, 1986 [JP] Japan ................................ 61-167304

[51] Int. Cl.⁴ .......................... A61B 6/03; G01N 23/08
[52] U.S. Cl. ........................................... 378/9; 378/10; 378/137
[58] Field of Search ..................... 378/4, 9, 10, 16, 137

[56] References Cited

U.S. PATENT DOCUMENTS

| 4,223,225 | 7/1980 | Laffitte et al. | 378/9 |
| 4,274,005 | 6/1981 | Yamamura et al. | 378/9 |
| 4,289,969 | 9/1981 | Cooperstein et al. | 378/9 |
| 4,592,079 | 5/1986 | Sohval et al. | 378/9 |

FOREIGN PATENT DOCUMENTS 2019688  4/1979  United Kingdom .................... 378/9

Primary Examiner—Carolyn E. Fields
Assistant Examiner—Joseph A. Hynds
Attorney, Agent, or Firm—Oblon, Fisher, Spivak, McClelland & Maier

[57] ABSTRACT

An X-ray CT scanner comprises a plurality of X-ray generators which are arranged radially on a circle concentric with an object for measurement and each consists of a cathode electrode, an anode electrode constituting a target and a grid between the cathode and anode electrodes. For X-ray tomography, X-rays are projected onto the objects from the circle concentric therewith by sequentially temporarily removing a bias voltage applied to the grids of the respective X-ray generators for suppressing an electron beam directed from the cathode electrode to the anode electrode of each X-ray generator.

2 Claims, 4 Drawing Sheets

ULTRAHIGH SPEED X-RAY CT SCANNER

BACKGROUND OF THE INVENTION

1. Field of the Invention

This invention relates to an ultrahigh speed X-ray CT scanner which can be suitably utilized for the observation of the dynamic state of human organs for the purpose of diagnosis and also for the measurement of flow with non-uniform density such as multiphase flow.

Description of the Prior Art

In the conventional X-ray CT scanner, X-ray sources are mechanically scanned on a circle concentrically surrounding the object and X-rays transmitted through an object are detected by X-ray sensors to obtain a section of the object. The mechanical scanning requires at least several seconds. Therefore, it is impossible to realize dynamic photographing of the object. Further, the CT scanner cannot be utilized for ascertaining dynamic changes of human organs or for dynamically ascertaining the state of flow of a fluid through pipe. Recently there has been developed an apparatus which permits obtaining one section in 30 to 50 milliseconds which incorporates high speed rotating X-ray source produced by electronically scanning a single electron beam. Theoretically, however, the electron beam scanning system inevitably leads to an increase in size and complexity of the system as a whole including accessory units, and also it is difficult to cause the electron beam to impinge on a target with high positional accuracy. (U. S. Pat. No. 4,352,021, IEEE Transaction on Nuclear Science, Vol, NS-26, No. 2, April 1979).

OBJECT AND SUMMARY OF THE INVENTION

An object of the present invention is to provide an X-ray CT scanner which has no movable parts and enables ultrahigh speed scanning with a very simple construction.

To attain the above object of the present invention, there is provided an X-ray CT scanner comprising a plurality of X-ray generators (sources) disposed on a circle concentrically surrounding an object for measurement and adapted to project X-rays onto the object, each of said X-ray generators including a cathode electrode, an anode electrode constituting a target and a grid disposed between said cathode and anode electrodes, and means for temporarily removing a bias voltage, applied to said grid to suppress an electron beam directed from said cathode electrode to said anode electrode, to generate and scan X-rays.

In the presence of a high voltage applied between the cathode and anode electrodes to obtain X-rays having the required intensity, a bias voltage, which is applied to the individual grids of each of these X-ray generators to suppress an electron beam directed towards the anode electrode from the cathode electrode, is sequentially temporarily removed to obtain scanning X-rays. Since the electron beam on-off control is carried out electronically as described above, the scanning of the X-ray can be conducted continuously at an ultrahigh speed of 10 milliseconds or less per one section, thus permitting to obtain a time-dependent sectional view so that the dynamic state of the object to be ascertained accurately.

The above and other objects and features of the invention will become more apparent from the following detailed description with reference to the accompanying drawings.

DETAILED DESCRIPTION OF THE PREFERRED EMBODIMENTS

Figure 1:
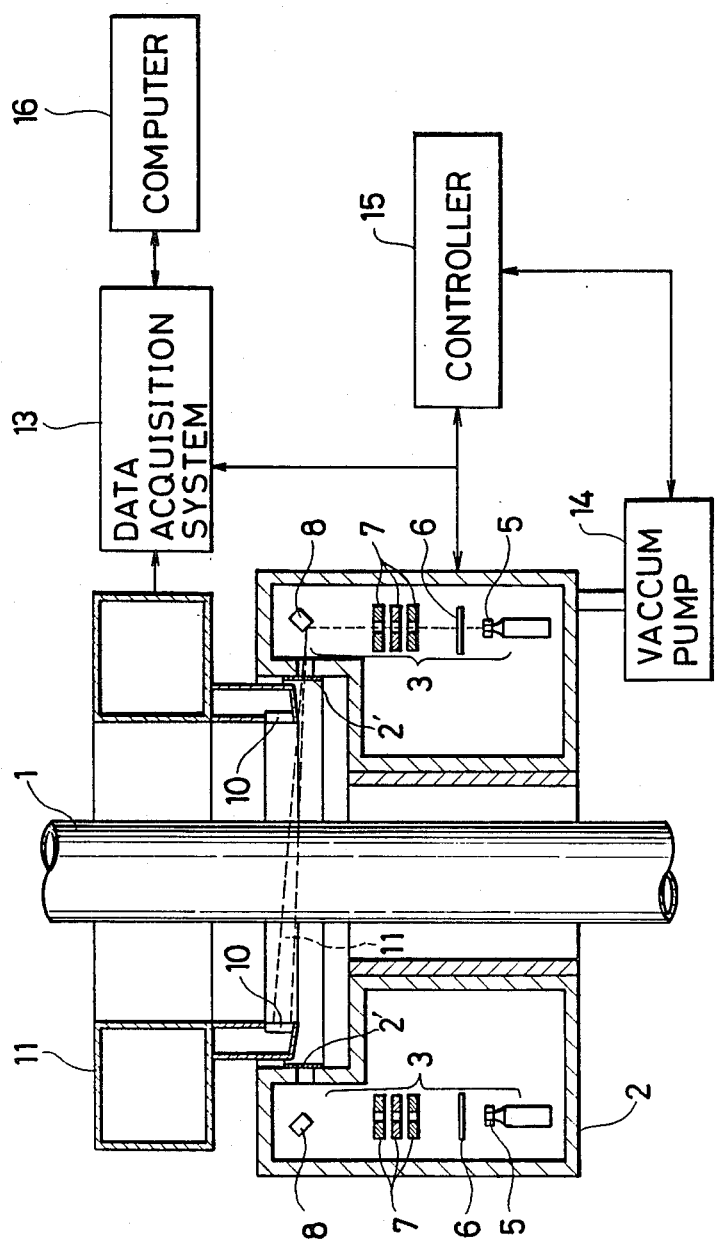
FIG. 1 is a schematic sectioned view showing of a first embodiment of the X-ray CT scanner according to the present invention.
Figure 2:
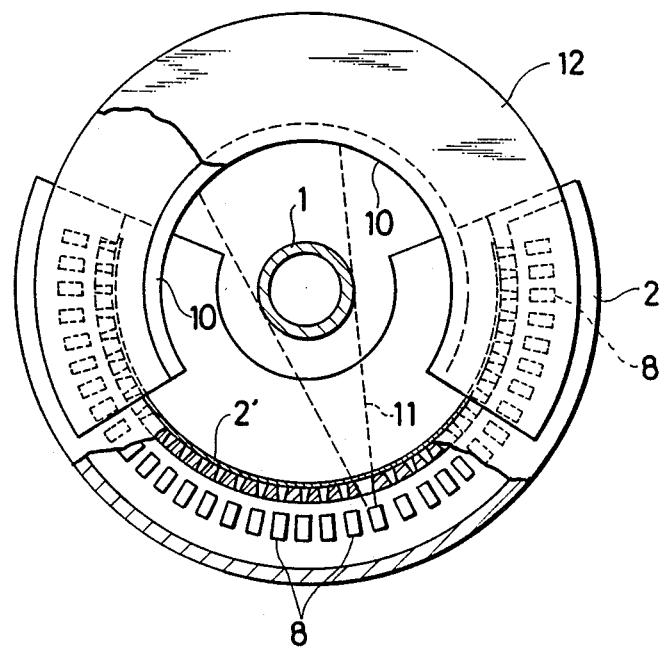
FIG. 2 is a plan view, partly broken away, showing the CT scanner shown in FIG. 1.

FIGS. 1 and 2 illustrate an embodiment of the ultrahigh speed X-ray CT scanner according to the present invention. A plurality of X-ray generators 3 in the number needed for obtaining the projection data necessary to reconstruct an image with required resolution are provided at predetermined intervals on a semi circle concentrically surrounding a pipe 1 for measuring the flow pattern of a multiphase flow inside the pipe. The X-ray generators 3 are provided in a ring-like vacuum vessel 2 connected to a vacuum pump 14. Each X-ray generator 3 provided in the vacuum vessel 2 consists of a cathode electrode 5, a grid 6, an accelerating electrode 7 which also serves as a convergent lens and consists of a number of stages, and a tungsten target 8 constituting an anode electrode. The constituent elements of the X-ray generator are arranged such that the trajectory of an electron beam is substantially parallel to the axis of the pipe 1. When a voltage for obtaining X-rays having the required intensity is applied between the cathode and anode electrodes, the electron beam that is generated in the cathode electrode strikes the target 8 constituting the anode electrode and X-rays are emitted from the target. The X-ray beam 11 is thus projected through an aluminum window 2' onto the periphery of the pipe 1.

A high voltage of about 100 KV, for example, for acceleration is applied between the cathode and anode electrodes. When the high voltage is merely applied between the two electrodes, a discharge is liable to occur in the vacuum vessel 2. The multi-stage accelerating electrode 7 is provided for dividing the high voltage into a plurality of voltages for acceleration instead of accelerating the electron beam at one time with the high voltage between the cathode and anode electrodes. Further, each accelerating electrode is provided to function as a convergent lens to enhance the utilization efficiency of the beam.

In each X-ray generator 3, the grid 6 which is provided between the cathode electrode 5 and target 8 is connected to an X-ray generator controller 15. The X-ray generator controller 15 controls a grid bias voltage in the X-ray generator 3 to electrically scan the point of generation of X-rays provided on the circle concentric with the pipe 1. The time required to obtain projection data for one section of the object is less than 10 milliseconds.

More specifically, after evacuating the vacuum vessel 2 to a predetermined vacuum degree by operating the vacuum pump 14 according to a command from the X-ray generator controller 15, a voltage for obtaining X-rays having the required intensity is applied between the cathode and anode electrodes, thus applying a grid bias voltage to the grid 6 in each X-ray generator 3 for suppressing the electron beam from the cathode electrode to the anode electrode. Then, the grid bias voltages applied to the grids 6 in the respective X-ray generators 3 are temporarily removed one after another under control of the X-ray generator controller 15. Then, X-rays 11 are generated by an electron beam impinging on the anode electrode to be projected onto the pipe 1. Since there is no mechanically movable part, by sequentially effecting the removal of the grid bias voltage in the respective X-ray generators 3 provided on a semi circle concentric with the subject 1, it is possible to obtain the projection data at an ultrahigh speed of less than 1 millisecond per one section if the subsequent signal processing speed is sufficiently increased.

X-rays projected toward the pipe 1 from the semi-circle surrounding the pipe 1 are detected by a plurality of X-ray sensors 10, which are provided on the inner periphery of a substantially semi-circular support and consist of scintillators and photodiodes. The detection signals are transferred to a data acquisition system 13 which is connected to the X-ray sensors 10. After predetermined X-ray scanning cycles have been completed, these signals are supplied to a computer 16, whereby an image of the section of the object is reconstructed.

Figure 3:
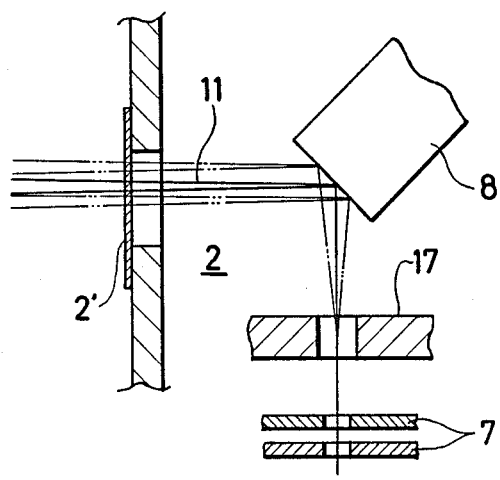
FIG. 3 is an enlarged essential view showing a modification of the CT scanner shown in FIG. 1.

FIG. 3 shows a modification of the CT scanner shown in FIG. 1. In this instance, a beam deflector 17 is provided between the multi-stage accelerating electrode 7 and the anode electrode 8 as a target of the X-ray generator.

By supplying a control signal to the beam deflector 17 the electron beam accelerated by the accelerating electrode may be deflected in a predetermined direction to impinge on a different portion of the target 8 as shown by the chain lines. In this way, the location onto which the X-rays 11 are projected can be varied without causing any movement of the object 1.

Thus, multi-layer X-rays may be generated by the application of a bias voltage to the grid 6 and control of a command signal supplied to the beam deflector 17, so that it is possible to obtain a three-dimensional tomographic image of the object. The electron beam deflection control may be carried out either with an electric field or with a magnetic field.

Figure 4:
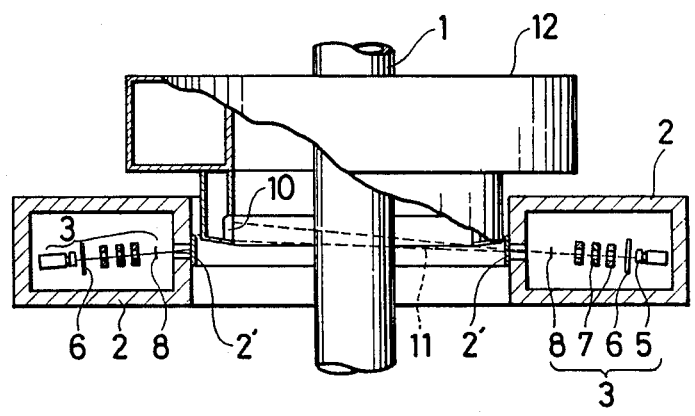
FIG. 4 is a schematic side view, partly in section, showing a second embodiment of the CT scanner according to the present invention.
Figure 5:
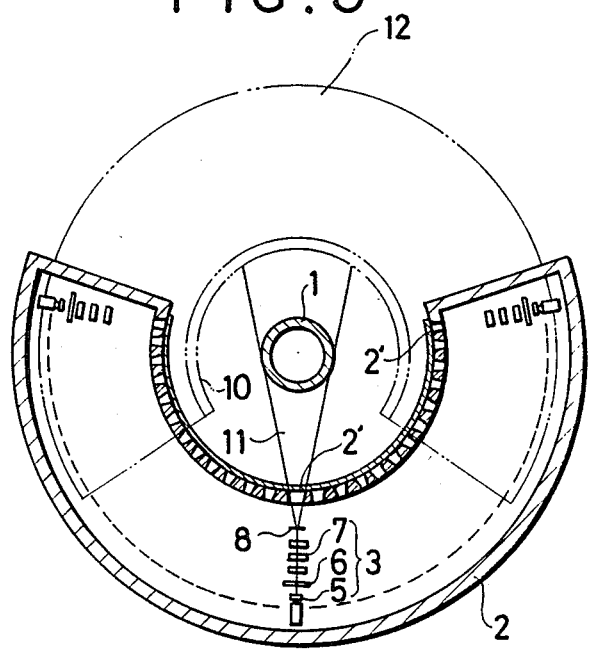
FIG. 5 is a plan view, partly broken away, showing X-ray generators in the CT scanner shown in FIG. 4.

FIGS. 4 and 5 illustrate a second embodiment of the CT scanner according to the invention. In a vacuum vessel 2, a predetermined number of X-ray generators 3 are arranged radially with respect to an object for measurement 1. A target 8 in each X-ray generator is in the form of a thin film having a thickness equal to or less than the range of the accelerated electron beam, and it is disposed on the electron beam path. Thus, X-rays 11 are emitted in the same direction as the direction of progress of the electron beam, and the CT scanner serves as a transmitting X-ray type CT scanner.

With the radial arrangement of the plurality of X-ray generators in the vacuum vessel 2, which is substantially semi-circular, with respect to the object 1 for measurement as in this modification, it is ready to select a large pitch of mounting of the X-ray generators. Thus, this modification of the CT scanner is effective where an electron beam accelerated by a high acceleration voltage is necessary and may be used for non-destructive inspection of metal components having large thicknesses.

Now, an example of the invention will be described. In the CT scanner having a construction as shown in FIGS. 1 and 2, a substantially semi-circular vacuum vessel was used, which included 35 X-ray generators arranged at a pitch of 6 degrees. Each X-ray generator had a thermoelectron emission filament (cathode), a grid, a three-stage beam acceleration/converging electrode and a tungsten target (anode). Each X-ray generator was for generating a fan beam X-ray collimated to have a center angle of 24 degrees. As the sensor was used a combination of a $CdWO_4$ scintillator and a silicon photodiode. 122 sensors were arranged over the inner periphery of a substantially semi-circular support subtending an angle of 246 degrees such that 32 sensors received each X-ray beam. As the object for a performance test was used one obtained by inserting three acrylic solid pipes 10 mm in diameter into an acrylic pipe 50 mm in outer diameter and 5 mm in thickness. The object was disposed at the center of the CT scanner.

The vacuum vessel was evacuated to a vacuum degree of approximately $10^{-6}$ Torr, and then a voltage of 100 KV was applied between the cathode and anode electrodes. Then, the bias on the grid of the X-ray generators was sequentially and temporarily removed with a pulse having a duration of approximately 250 msec. generated with a control pulse start signal as a trigger signal. As a result, an electron beam was caused to impinge on 35 targets sequentially to generate X-rays, which were transmitted through a collimator and projected onto the object through an aluminum window with a thickness of 0.5 mm.

Output signals from the 122 X-ray generators were all converted into digital signals and stored in the data acquisition system in synchronism to an X-ray generator grid control pulse.

Figure 6:
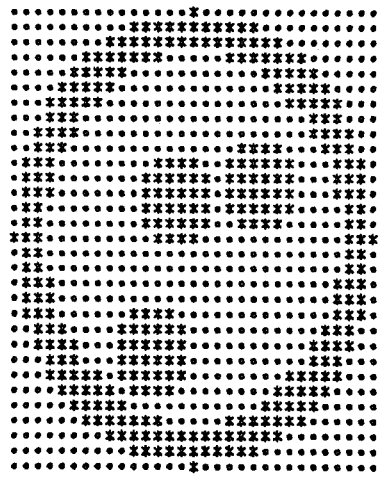
FIG. 6 is a view showing an image reconstructed using data obtained with the CT scanner according to the present invention.

The scanning time for 35 X-ray generators was approximately 10 msec. The resultant X-ray absorption data was transferred a computer to reconstruct an image with respect to a 31-by-31 matrix by the ART method. The result is as shown in FIG. 6. The image was drawn according to a line printer output of the computer, so that it was slightly vertically elongated. In FIG. 4, portions corresponding to acryle are represented by asterisks, and those corresponding to the air space are represented by dots. In the above section pattern, the position of the solid pipe of the object was accurately reproduced with a resolution of 2 mm or lower. Further, in contrast to an actually measured void fraction (sectional area of air portion divided by total sectional area) of 52%, the calculated value of void fraction based on the results of measurement using the CT scanner was 55.5%, i.e., higher by approximately 3% than the actual value. However, it is thought that a more accurate value can be obtained by increasing the number of matrix pixels by increasing the number of X-ray generators and X-ray sensors.

As has been described in the foregoing, the ultrahigh speed X-ray CT scanner according to the invention not only permits dynamic photographing of organs through electronic high speed scanning of the point of generation of X-rays, but can also be utilized for industrial purposes, e.g., measurement of flow. Further, it is possible to provide a very compact CT scanner construction. Further, since with the X-ray CT scanner according to the invention the X-ray generators and sensors are disposed in an independent, substantially semi-circular ring-like vessel, the CT scanner according to the invention can be readily installed on a stationary object, such as on nuclear reactor piping, for accurate measurement of the dynamic state of the fluid in the pipe or for non-destructive inspection of the piping material.

What is claimed is:

1. An ultrahigh-speed X-ray CT scanner comprising:
   a substantially semicircular vacuum vessel disposed on a circumference of a circle concentrically surrounding a position for an object for measurement;
   a plurality of X-ray generators disposed in said vacuum vessel and arranged on the circumference of the circle for projecting X-rays onto said object, each of said X-ray generators including a cathode electrode, a grid, a multi-stage electrode for converging and accelerating an electron beam emitted from said cathode electrode, and an anode electrode constituting a target;
   means for applying a bias voltage to the grids,
   means for temporarily removing the bias voltage applied to said grids one after another; and
   a plurality of X-ray sensors supported by a substantially semicircular support which is disposed on the circumference of the circle at a position where said object intervenes between said sensors and said vacuum vessel, and arranged on the circumference of the circle for receiving the X-rays projected from said X-ray generators wherein each of said x-ray generators includes a beam deflection lens disposed between said multi-stage electrode and said target so as to deflect the electron beam in the axial direction of the object.

2. The X-ray CT scanner according to claim 1, wherein said target is formed of a film having a thickness equal to or less than the range of the electron beam accelerated.

* * * * *